US00PP36989P2

(12) United States Plant Patent
Verschoor

(10) Patent No.: US PP36,989 P2
(45) Date of Patent: Sep. 30, 2025

(54) ***ACHILLEA* PLANT NAMED 'Versred'**

(50) Latin Name: *Achillea millefolium*
Varietal Denomination: Versred

(71) Applicant: Janus Verschoor, Haarlem (NL)

(72) Inventor: Janus Verschoor, Haarlem (NL)

(73) Assignee: A. VERSCHOOR HORTICULTURE, Haarlem (NL)

( * ) Notice: Subject to any disclaimer, the term of this patent is extended or adjusted under 35 U.S.C. 154(b) by 0 days.

(21) Appl. No.: 19/098,717

(22) Filed: Apr. 2, 2025

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Achillea* plant named 'Versred' that is characterized by its very floriferous flowering habit with continuous bloom throughout the growing season, its bright red flowers when mature, its inflorescences that are large in size with a high quantity of flowers per inflorescence, its compact a plant habit with no plant growth regulators required, its sturdy stems, and its suitability for growing well in containers.

3 Drawing Sheets

Botanical classification: *Achillea millefolium.*
Variety denomination: 'Versred'.

BACKGROUND OF THE INVENTION

The present invention relates to a new and distinct cultivar of *Achillea millefolium* origin named 'Versred', and is hereinafter referred to by its cultivar name 'Versred'. 'Versred' is a new cultivar of yarrow, a hardy perennial grown for landscape use.

The new cultivar arose from an ongoing breeding program in Haarlem, The Netherlands. The goal of the breeding program was to develop new cultivars of *Achillea* with strong flower colors, compact plant habits, and disease resistance. The Inventor collected and sowed seeds from open pollination of numerous proprietary seedlings and cultivars from the Inventor's breeding program. The seeds were pooled prior to sowing, the parentage of 'Versred' is therefore unknown. The new cultivar was selected as a single unique plant from the resulting seedlings in 2016.

Asexual propagation of the new cultivar was first accomplished under the direction of the Inventor by division in 2019 in Haarlem, The Netherlands. Asexual propagation of the new cultivar by division and tissue culture using meristematic has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Versred' as a new and unique cultivar of *Achillea.*

1. 'Versred' exhibits a very floriferous flowering habit with continuous bloom throughout the growing season.
2 'Versred' exhibits bright red flowers when mature.

3. 'Versred' exhibits inflorescences that are large in size with a high quantity of flowers per inflorescence.
4. 'Versred' exhibits a compact a plant habit with no plant growth regulators required.
5. 'Versred' exhibits sturdy stems.
6. 'Versred' exhibits suitability for growing well in containers.

'Versred' can be most closely compared to the *Achillea* cultivars 'Red Velvet' (not patented), 'Sparkling Contrast' (not patented), and 'Verspink' (not patented). 'Red Velvet' is similar to 'Versred' in having inflorescences that are red in color. 'Red Velvet' differs from 'Versred' in having a taller plant height, a less continuously flowering habit, and a plant habit that falls open. 'Sparkling Contrast' is similar to 'Versred' in having red flowers. 'Sparkling Contrast' differs from 'Versred' in having a less continuously flowering habit and a taller plant height. 'Verspink' is similar to 'Versred' in plant and blooming habit. 'Verspink' differs from 'Versred' in having pink colored flowers.

BRIEF DESCRIPTION OF THE DRAWINGS

The accompanying color photograph illustrates the overall appearance and distinct characteristics of the new *Achillea*. The photographs were taken of a plant 12 weeks in age as grown outdoors in a 17-cm container in Waddinxveen, The Netherlands.

The photograph in FIG. 1 provides a side view of the plant of 'Versred' in bloom.

Figure 1:
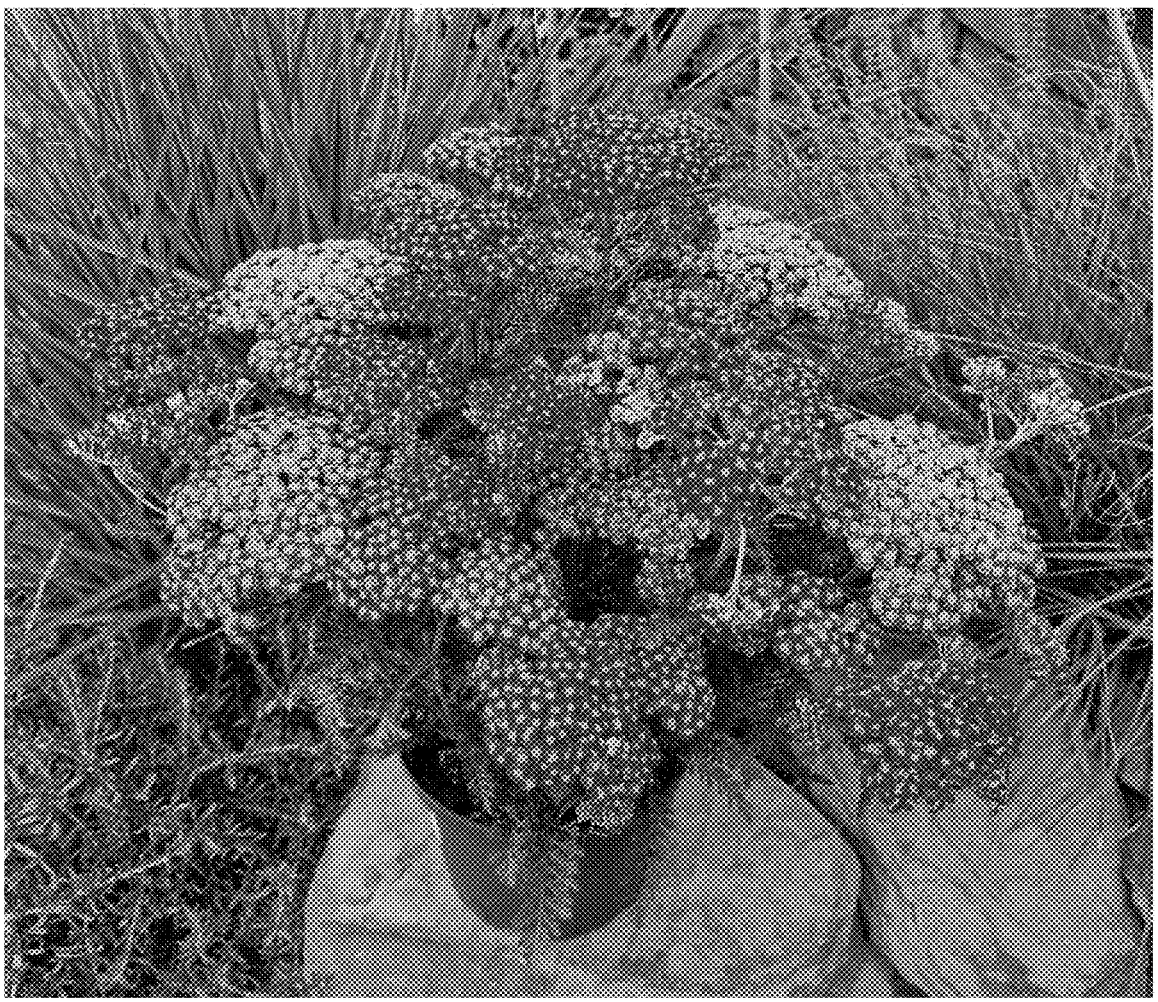
Figure 2:
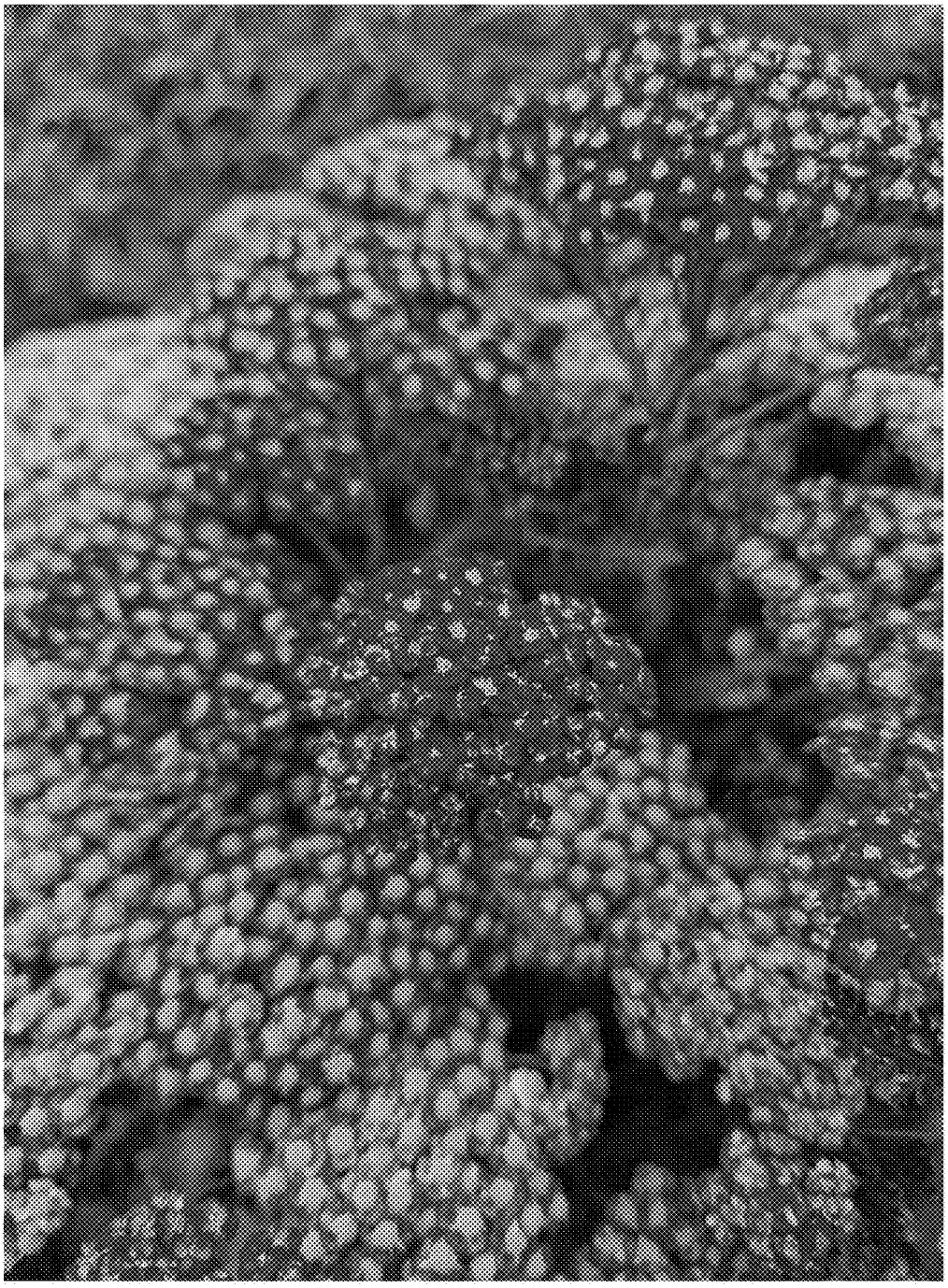

The photograph in FIG. 2 provides a close-up of the inflorescences of 'Versred'.

Figure 3:
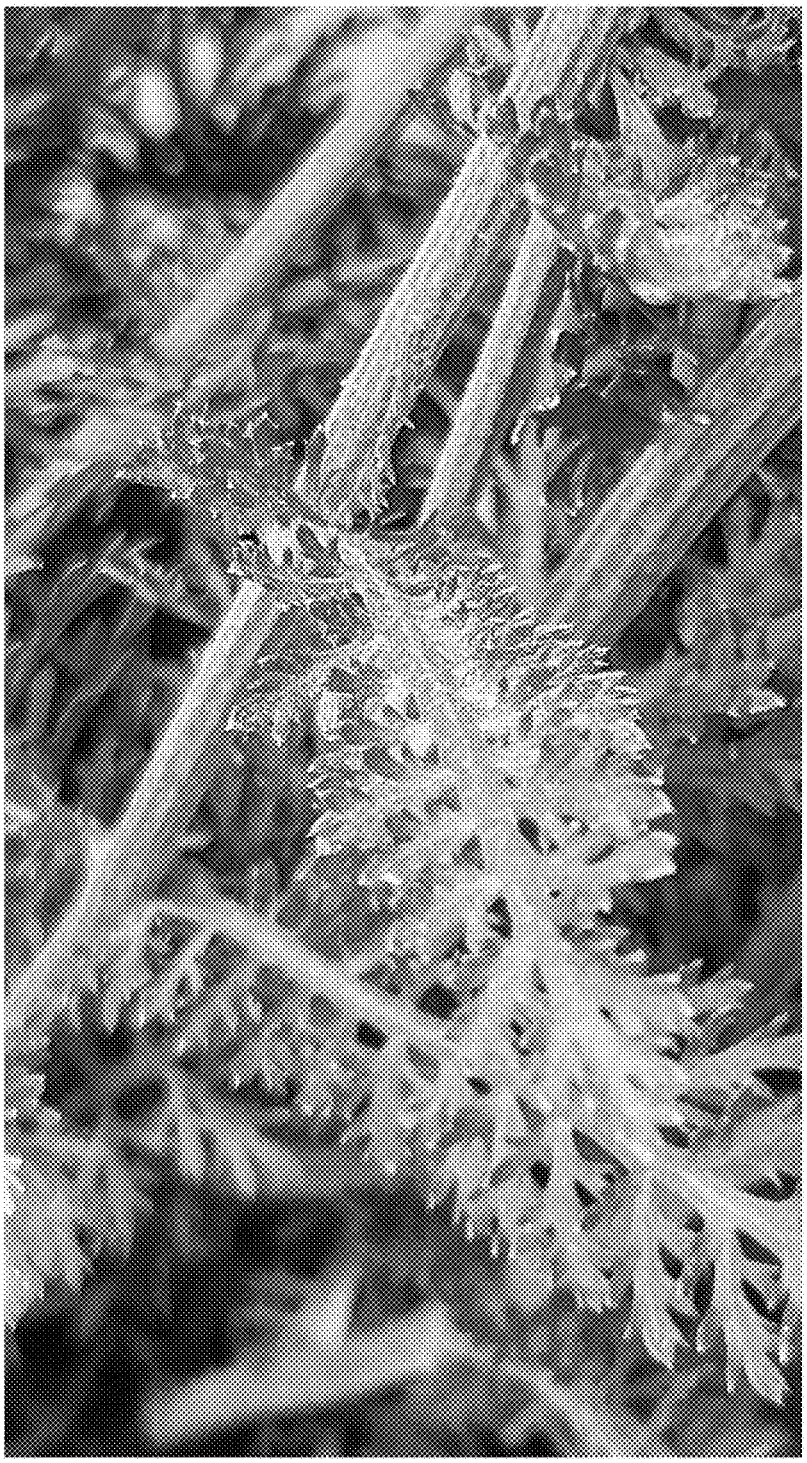

The photograph in FIG. 3 provides a close-up view of the foliage and stems of 'Versred'.

The colors in the photograph are as close as possible with the digital photography techniques available, the color values cited in the detailed botanical description accurately describe the colors of the new *Achillea.*

DETAILED BOTANICAL DESCRIPTION

The following is a detailed description of 12-week-old plants of the new cultivar as grown outdoors in 17-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms throughout summer in The Netherlands.

*Plant type*.—Herbaceous perennial.

*Plant habit*.—Compact, upright spreading, non-lodging in full bloom.

*Height and spread*.—An average of 37 cm in height and 43 cm in width as a one-ye old plant grown in a container.

*Hardiness*.—At least in U.S.D.A. Zones 3 to 8.

*Diseases and pests*.—No susceptibility or resistance to diseases or pest has been observed.

*Root description*.—Fibrous.

*Propagation*.—Tissue culture and division.

*Root development*.—21 to 24 days for root initiation, 12 weeks to produce a young plant in a 12-cm container.

*Growth rate*.—Vigorous.

Stem description:

*Shape*.—Round.

*Stem color*.—137C in color.

*Stem size*.—Up to 22 cm in length and 6 mm in diameter.

*Stem surface*.—Pubescent, covered with soft hairs on immature stems and sparse hairs on mature stems.

*Branching habit*.—Compact and freely branching.

*Stem number*.—Average of 18 per plant.

*Internode length*.—Up to 2.5 cm in length.

Foliage description:

*Leaf division*.—Simple.

*Leaf shape*.—Lanceolate to linear.

*Leaf base*.—Attenuate.

*Leaf apex*.—Acute.

*Leaf margin*.—Serrate.

*Leaf venation*.—Only midrib is visible, upper surface matches leaf color, lower surface 144B in color.

*Leaf quantity*.—Average of 12 per lateral branch.

*Leaf attachment*.—Sessile.

*Leaf arrangement*.—Alternate.

*Leaf surface*.—Upper surface slightly glossy, lower surface pubescent; more so on the young leaves.

*Leaf color*.—Young and mature upper surface; 137A, young and mature lower surface; 137B.

*Leaf size*.—Average of 14.8 cm in length and 5 cm in width.

Flower description:

*Inflorescence type*.—Composite on terminal and upper nodes of stems.

*Inflorescence size*.—Up to 15 cm in height and 6 cm in width.

*Inflorescence quantity*.—Average of 23.

*Lastingness of inflorescence*.—About 7 to 10 days until senescence of ray flowers. Bracts and disk flowers are persistent.

*Flower fragrance*.—None.

*Flower buds*.—3 mm in length, 2 mm in diameter, round in shape, color; 137D with petal portion 8C.

*Phyllaries*.—Up to 4 mm in length and 1.5 mm in diameter, acute apex, truncate base, 137C to 137D in color on both surfaces, outer surface sparsely pubescent with long, thin hairs, inner surface glabrous.

*Peduncle*.—Up to 1.5 cm in length and 1.5 mm in diameter, 137C to 137D in color, surface is sparsely pubescent.

*Pedicel*.—None.

*Receptacle*.—Not distinct, small, chaffy, 144A in color.

Ray florets:

*Number*.—5.

*Shape*.—Orbicular.

*Size*.—Average of 3 mm in length and 4 mm in width.

*Petal apex*.—Emarginate.

*Petal base*.—Attenuate.

*Petal margins*.—Entire.

*Petal texture*.—Smooth.

*Color*.—Young upper surface; 2B with margins 60A, young lower surface; 2C with pale margins 60A, mature upper surface; 60A, mature lower surface; 2D with 60C edges 60A.

Disk flowers:

*Quantity*.—25 to 30.

*Shape*.—Narrow funnel-shaped.

*Size*.—Average of 3 mm in length and up to 1 mm in width.

*Apex*.—Acute.

*Base*.—Tubular.

*Color*.—2B to 2D.

Reproductive organs:

*Gynoecium*.—Pistil; 1 per floret, 2-lobed, up to 2 mm in length, stigma; 2D in color, style; average of 4 mm in length, 1 mm in diameter, 157D in color, ovary; very small, 145D in color.

*Androecium*.—Stamens; one per floret, filament; 2 mm in length, 1 mm in diameter and 145B in color, anther, 9A in color, pollen; moderate in quantity, 9A in color.

*Fruit and seed*.—None observed to date.

It is claimed:

1. A new and distinct cultivar of *Achillea* plant named 'Versred' as herein illustrated and described.

* * * * *